United States Patent [19]

Kabbe et al.

[11] Patent Number: 4,647,579

[45] Date of Patent: Mar. 3, 1987

[54] CIRCULATION ACTIVE NOVEL SUBSTITUTED 4-HYDROXY-BENZOPYRANS

[75] Inventors: Hans-Joachim Kabbe, Leverkusen; Arno Widdig, Odenthal; Ulrich Niewöhner, Wermelskirchen; Andreas Knorr, Wuppertal; Bernward Garthoff, Hilden; Stanislav Kazda, Wuppertal, all of Fed. Rep. of Germany

[73] Assignee: Bayer Aktiengesellschaft, Leverkusen, Fed. Rep. of Germany

[21] Appl. No.: 714,340

[22] Filed: Mar. 21, 1985

[30] Foreign Application Priority Data

Mar. 31, 1984 [DE] Fed. Rep. of Germany ....... 3411992

[51] Int. Cl.$^4$ ..................... A61K 31/35; C07D 311/22
[52] U.S. Cl. .................................. 514/456; 549/401; 549/345; 549/332
[58] Field of Search ................ 549/401, 345; 514/456; 424/14

[56] References Cited

PUBLICATIONS

Daiichi, Chem. Abstr., 101, 191691n, (1984).
Kabbe et al., ibid., 102, 6203q, (1984).

*Primary Examiner*—Nicky Chan
*Attorney, Agent, or Firm*—Sprung Horn Kramer & Woods

[57] ABSTRACT

Novel substituted 4-hydroxy-benzopyrans of the formula

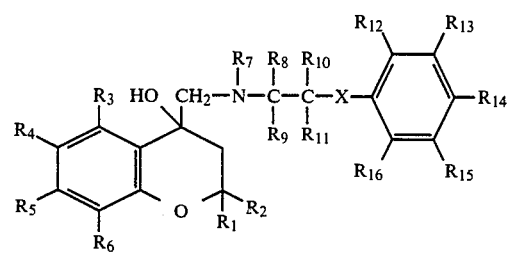

in which
X is a single bond,

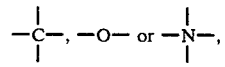

and the other radicals can have various meanings, or pharmaceutically acceptable addition salts thereof, which are active on the circulation system.

13 Claims, No Drawings

CIRCULATION ACTIVE NOVEL SUBSTITUTED 4-HYDROXY-BENZOPYRANS

The present invention retates to substituted 4-hydroxy-benzopyrans, several processes for their preparation, and their use in medicaments, in particular in agents which influence the circulation.

The new compounds can be represented by the following formula (I):

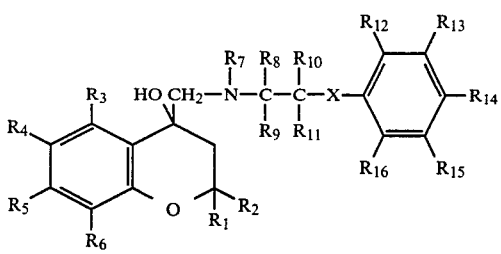

in which $R_1$ and $R_2$ are identical or different and represent hydrogen, alkyl, cycloalkyl, optionally substituted aryl or optionally substituted aralkyl, or in which $R_1$ and $R_2$, together with the carbon atom between them, form a carbocyclic ring, $R_3$, $R_4$, $R_5$ and $R_6$ are identical or different and represent hydrogen, hydroxyl, halogen, alkyl, cycloalkyl, optionally substituted aryl, optionally substituted aralkyl, alkoxy, optionally substituted aryloxy and optionally substituted aralkoxy, $R_7$, $R_8$, $R_9$, $R_{10}$ and $R_{11}$ are identical or different and represent hydrogen or alkyl, X represents a single bond, or methylene which is optionally substituted by one or two alkyl groups, or represents oxygen or $NR_{17}$, wherein $R_{17}$ represents hydrogen and alkyl having up to 6 carbon atoms or $R_{17}$, together with $R_7$, represents $C_2$-$C_3$-alkylene, $R_{12}$, $R_{13}$, $R_{14}$, $R_{15}$ and $R_{16}$ are identical or different and each represent hydrogen, hydroxyl, halogen, alkyl, cycloalkyl, alkoxy, aralkoxy, trifluoromethyl, nitro, cyano or the

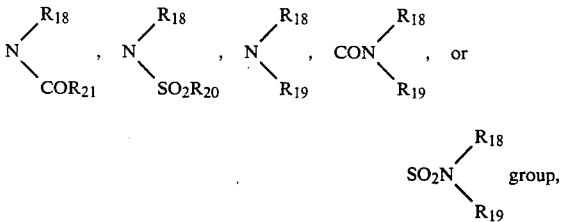

wherein $R_{18}$ and $R_{19}$ are identical or different and each represent hydrogen or optionally substituted alkyl, and wherein $R_{20}$ represents optionally substituted alkyl, and wherein $R_{21}$ represents hydrogen, optionally substituted alkyl, optionally substituted alkoxy or optionally substituted alkylamino, and $R_{12}$ and $R_{13}$ or $R_{13}$ and $R_{14}$ together optionally each represent an alkylenedioxy group or the group —CH=CH—CH=CH—, or wherein $R_{18}$ together with $R_{19}$ or together with $R_{20}$ or together with $R_{21}$ can form a 5-membered to 7-membered heterocyclic ring which contains an alkylene bridge having 2 to 5 carbon atoms and optionally also contains an additional carbonyl group, and their pharmaceutically acceptable addition salts.

Preferred alkyl radicals in the substituents $R_1$–$R_{21}$ are straight-chain or branched $C_1$-$C_{18}$-alkyl radicals, preferably $C_1$-$C_{12}$-alkyl radicals, in particular $C_1$-$C_6$-alkyl radicals, unless stated otherwise in the text.

The following may be mentioned as examples of alkyl radicals: methyl, ethyl, propyl, isopropyl, butyl, isobutyl, tert.-butyl, hexyl, 2-hexyl, 1,1-dimethylpentyl, 1,1-dimethylhexyl, nonyl, decyl, undecyl and tetradecyl.

Preferred cycloalkyl radicals in the radicals $R_1$, $R_2$, $R_3$, $R_4$, $R_5$, $R_6$ and $R_{12}$ to $R_{16}$ are those having 3–18, preferably 4–12, particularly preferably 5 and 6 carbon atoms, such as, for example, cyclopropyl, cyclobutyl, cyclopentyl, cyclohexyl, cycloheptyl, cyclooctyl, cyclododecyl, cycloheptadecyl and cyclooctadecyl, particularly preferably cyclopentyl and cyclohexyl.

Preferred optionally substituted alkyl radicals in the radicals $R_{12}$–$R_{21}$ are alkyl groups which are monosubstituted, disubstituted or trisubstituted by hydroxyl, halogen, in particular fluorine or chlorine, cyano, nitro, alkoxy having 1 to 4 C atoms or trifluoromethoxy.

Optionally substituted aryl radicals in the radicals $R_1$, $R_2$ and $R_3$ to $R_6$ are aryl having preferably 6 to 10 carbon atoms in the aryl part. Optionally substituted phenyl and naphthyl may be mentioned as examples.

Preferred optionally substituted aralkyl radicals in the radicals $R_1$, $R_2$ and $R_3$ to $R_6$ are those which have 7 to 18 carbon atoms and the aliphatic part of which contains 1 to 8, preferably 1 to 4, carbon atoms and the aromatic part of which is a carbocyclic radical having 6 to 10 carbon atoms. The following aralkyl radicals may be mentioned as examples: benzyl, phenylethyl, phenylpropyl, phenylbutyl and naphthylmethyl, preferably benzyl.

Alkoxy radicals in the radicals $R_3$ to $R_6$ and $R_{12}$ to $R_{21}$ are straight-chain or branched alkoxy having preferably 1 to 6, in particular 1 to 4, carbon atoms. Methoxy, ethoxy, n- and i-propoxy and n-, i- and t-butoxy may be mentioned as examples. Preferred aryloxy groups $R_3$ to $R_6$ and $R_{12}$ to $R_{16}$ which may be mentioned are those having 6 or 10 carbon atoms, such as phenoxy or naphthoxy.

Aralkoxy radicals in the radicals $R_3$ to $R_6$ which may be mentioned are those having preferably 7 to 10 carbon atoms, such as benzyloxy, phenylethoxy, phenylpropoxy, phenylisopropoxy, phenylbutoxy and phenylisobutoxy.

Fluorine, chlorine, bromine and iodine, preferably fluorine, bromine and chlorine, may be mentioned as halogens in the radicals $R_3$ to $R_6$ and $R_{12}$ to $R_{21}$.

If the radicals $R_1$ and $R_2$, together with the carbon atom between them, form a carbocyclic ring, suitable rings are 3-membered to 12-membered rings, preferably 4-membered to 7-membered rings. The following may be mentioned as examples of carbocyclic radicals: cyclopropane, cyclobutane, cyclopentane, cyclohexane, cycloheptane, cyclononane, cyclodecane and cyclododecane.

Suitable substituents of the aryl, aralkyl, aryloxy and aralkoxy radicals $R_1$ to $R_6$ are substituents which are not changed under the reaction conditions. The halogens, such as fluorine, chlorine, bromine and iodine, the $C_1$–$C_6$-alkyl group, the $C_1$–$C_6$-alkoxy group and the trifluoromethyl group may be mentioned as examples.

The following may be mentioned as examples of acids for the preparation of the salts: sulphuric acid, hydrochloric acid, organic carboxylic acids, such as malic acid, citric acid, fumaric acid, maleic acid, succinic acid or acetic acid, or organic sulphonic acids, such as naphthalene-1,5-disulphonic acid.

The salts of the compounds of the formula (I) can be obtained in a simple manner by customary salt formation methods, for example by dissolving the base and adding the acid, and can be isolated in a customary manner, for example by filtration, and, if required, purified.

In formula (I):

$R_1$ and $R_2$ are identical or different and preferably represent hydrogen, $C_1$–$C_6$-alkyl, $C_5$–$C_7$-cycloalkyl, phenyl, optionally substituted (disubstituted, in particular monosubstituted) by $C_1$–$C_4$-alkyl, halogen (chlorine or bromine) and/or $C_1$–$C_4$-alkoxy, or $C_7$–$C_9$-aralkyl, the aryl radical of which is optionally substituted (monosubstituted or disubstituted, in particular monosubstituted) by $C_1$–$C_4$-alkyl, halogen (chlorine and bromine) and/or $C_1$–$C_4$-alkoxy, or $R_1$ and $R_2$, together with the included C atom of the chroman ring, form a 4- to 7-membered carbocyclic ring;

$R_3$ to $R_6$ are identical or different and preferably represent hydrogen, hydroxyl, halogen (chlorine or bromine), $C_1$–$C_6$-alkyl, $C_5$–$C_7$-cycloalkyl, phenyl, optionally substituted (monosubstituted or disubstituted, in particular monosubstituted) by $C_1$–$C_4$-alkyl, halogen (chlorine or bromine) and/or $C_1$–$C_4$-alkoxy, or $C_7$–$C_9$-aralkyl, the aryl radical of which is optionally substituted (monosubstituted or disubstituted, in particular monosubstituted) by $C_1$–$C_4$-alkyl, halogen (chlorine or bromine) and/or $C_1$–$C_4$-alkoxy; $R_7$, $R_8$, $R_9$, $R_{10}$ and $R_{11}$ are identical or different and represent hydrogen or $C_1$–$C_6$-alkyl, X represents a single bond or methylene, optionally monosubstituted or disubstituted by $C_1$–$C_4$-alkyl, or represents oxygen or —$NR_{17}$, wherein $R_{17}$ represents hydrogen or $C_1$–$C_4$-alkyl, or $R_{17}$ together with $R_7$ forms a $C_2$-alkylene ring closure, $R_{12}$, $R_{13}$, $R_{14}$, $R_{15}$ and $R_{16}$ are identical or different and each represent hydrogen, hydroxyl, chlorine, fluorine, alkyl having 1–4 C atoms, alkoxy having 1 to 3 C atoms, aralkoxy having up to 8 C atoms, trifluoromethyl, nitro, cyano or the

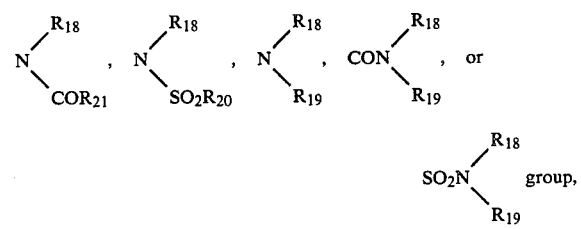

wherein $R_{18}$ and $R_{19}$ are identical or different and each represent hydrogen or alkyl having 1–4 C atoms which is optionally monosubstituted to trisubstituted by halogen, $R_{20}$ represents alkyl having 1–6 C atoms which is optionally monosubstituted to trisubstituted by halogen, $R_{21}$ represents hydrogen, alkyl, alkoxy or alkylamino, each having 1–4 C atoms per alkyl and alkoxy group, the alkyl radical being optionally monosubstituted to trisubstituted by halogen, and $R_{12}$ and $R_{13}$ or $R_{13}$ and $R_{14}$ together optionally represent an alkylenedioxy group having 1 or 2 C atoms or the —CH=CH—CH=CH— group, or wherein $R_{18}$ together with $R_{19}$ or together with $R_{20}$ or together with $R_{21}$ can form a 5-membered or 6-membered heterocyclic ring which contains an alkylene bridge having 2, 3 or 4 carbon atoms and also optionally contains an additional carbonyl group.

Particularly preferred compounds of the formula (I) are those
in which $R_1$ and $R_2$ are identical or different and represent hydrogen, $C_1$–$C_4$-alkyl, or, together with the carbon atom between them, form a carbocyclic $C_5$ or $C_6$ ring, $R_3$ to $R_6$ are identical or different and denote hydrogen, hydroxyl, $C_1$–$C_4$-alkyl, $C_1$–$C_4$-alkoxy or chlorine, $R_7$ to $R_{11}$ are identical or different and represent hydrogen or $C_1$–$C_4$-alkyl, X represents a single bond, oxygen, methylene or —$NR_{17}$,
wherein $R_{17}$ denotes hydrogen or $C_1$–$C_3$-alkyl, or wherein $R_{17}$ together with $R_7$ forms a ethylene ring closure, and $R_{12}$ to $R_{16}$ are identical or different and denote hydrogen, chlorine, cyclohexyl, $C_1$–$C_4$-alkyl, $C_1$–$C_3$-alkoxy, aralkoxy having 1–8 C atoms, trifluoromethyl, nitro, cyano or the

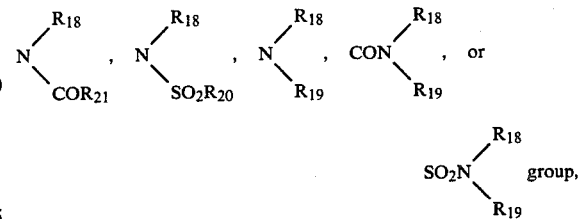

wherein $R_{12}$ and $R_{13}$ or $R_{13}$ and $R_{14}$ together each optionally form a methylenedioxy group or a —CH=CH—CH=CH— group,
and wherein $R_{18}$ and $R_{19}$ are identical or different and each represent hydrogen or alkyl having 1–4 C atoms which is optionally substituted by fluorine or chlorine,
and wherein $R_{20}$ represents alkyl having 1–4 C atoms which is optionally substituted by fluorine or chlorine,
and wherein $R_{21}$ represents hydrogen, optionally fluorine-substituted or chlorine-substituted alkyl having 1–4 C atoms, alkoxy or alkylamino, each having 1–2 C atoms.

The following may be mentioned as examples of new compounds of the general formula (I): 4-[N-(2-phenylethyl)-aminomethyl]-4-hydroxy-2,2-spirocyclopentachroman, 4-{N-[2-(3-chlorophenyl)-ethyl]-aminomethyl}-4-hydroxy-2,2-spirocyclohexachroman, 4-{N-[2-(4-methylphenyl)-ethyl]-aminomethyl}-4-hydroxy-2,2-dimethylchroman, 4-{N-[2-(3,4-methylenedioxyphenyl)-ethyl]-aminomethyl}-4-hydroxy-2,2-spirocyclopentachroman, 4-{N-[3-(3,4-dimethoxyphenyl)-propyl]-aminomethyl}-4-hydroxy-6,7-dimethyl-2,2-spirocyclopentachroman, 4-}N-[3-(4-trifluoromethylphenyl)propyl]-aminomethyl}-(-4-hydroxy-6-methoxychroman, 4-{N-[2-(3,4-dichlorophenoxy)-ethyl]-aminomethyl}-4-hydroxy-2,2-spirocyclohexachroman, 4-{N-[2-(3,4-dimethoxyphenoxy)-ethyl]-aminomethyl}-4-hydroxy-2,2-spirocyclopentachroman, 4-{N-[2-(3,4-methylenedioxyphenoxy)-isopropyl]-aminomethyl}-4-hydroxy-7-chloro-2,2-dimethylchroman, 4-{N-[4-(2-methylphenyl)-butyl]-aminomethyl}-4-hydroxy-2,2-spirocyclohexachroman, 4-{N-[4-(pentafluorophenyl)-butyl]-aminomethyl}-4-hydroxy-2,2-spirocyclopentachroman, 4-{N-[4-(3-chloro-5-methylphenyl)-butyl]-aminomethyl}-4-hydroxy-6,8-dimethylchroman, 4-{N-[4-(3,4-ethylenedioxyphenyl)-butyl]-aminomethyl}-4-hydroxy-2,2-spirocyclopentachroman, 4-{N-[4-(2-naphthyl)-butyl]-aminomethyl}-4-hydroxy-2,2-spirocyclopentachroman, 4-{N-[4-(3,5-dimethyl-4-methoxyphenyl)butyl]-aminomethyl}-4-hydroxy-2,2-dimethylchroman, 4-{N-[4-(3-carbomethoxy-5-methoxyphenyl)-butyl]-aminomethyl}-4-hydroxy-2,2-spirocyclohexachroman, 4-{N-[4-(3-methoxy-5-carbamoylphenyl)-butyl]-aminomethyl}-4-hydroxy-2,2-spirocyclopentachroman, 4-{N-[4-(3,4-methylenedioxy-5-carbamoylphenyl)-butyl]-aminomethyl}-4-hydroxy-2,2-spirocyclopentachroman, 4-{N-[4-(3-methyl-5-aminosulphonylphenyl)-butyl]-aminomethyl}-4-hydroxy-6,7-dimethyl-2,2-spirocyclohexachroman, 4-{N-[4-(3-chloro-5-aminosulphonylphenyl)-butyl]-aminomethyl}-4-hydroxy-2,2-dimethylchroman, 4-{N-[4-(3,4-methylenedioxy-5-aminosulphonylphenyl)-butyl]aminomethyl}-4-hydroxy chroman, 4-{N-[4-(3-aminophenyl)-butyl]-aminomethyl}-4-hydroxy-6-methoxy-2,2-spirocyclopentachroman, 4-{N-[4-(3-N,N-dimethylaminophenyl)-butyl]aminomethyl}-4-hydroxy-2,2-spirocyclopentachroman, 4-{N-[4-(3-succinimidophenyl)-butyl]-aminomethyl}-4-hydroxy2,2-spirocyclopentachroman, 4-{N-[4-(4-methylsulphonyaminophenyl)-butyl]-aminomethyl}-4-hydroxy-2,2-spirocyclopentachroman, 4-{N-[4-(3-ethylsulphonylaminophenyl)-butyl]aminomethyl}-4-hydroxy-2,2-spirocyclopentachroman, 4-{N-[4-(3-acetylaminophenyl)-butyl]-aminomethyl}-4-hydroxy-2,2-spirocyclopentachroman, 4-{N-[4-(4-cyanophenyl)-butyl]aminomethyl}-4-hydroxy-7-chloro-2,2-spirocyclopentachroman, 4-{N-[4-(3-pyrrolidinophenyl)-butyl]-aminomethyl}-4-hydroxy-2,2-dimethylchroman, 4-{N-[1-(3-nitrophenoxy)-isopropyl]-aminomethyl}-4-hydroxy-6,8-dimethyl-chroman, 4-{N-[1-(3-aminophenoxy)-isopropyl]-aminomethyl}-4-hydroxy-6,8-dimethyl-chroman, 4-{N-[1-(3-methylsulphonylphenoxy)-isopropyl]-aminomethyl}-4-hydroxy-6,8-dimethyl-chroman, 4-{N-[1-(3-N,N-dimethylaminosulphonylphenoxy)-isopropyl]-aminomethyl}-4-hydroxy-2,2-spirocyclopentachroman, 4-{N-[1-(4-carbamoylphenoxy)-isopropyl]-aminomethyl}-4-hydroxy-6,7-dimethyl-2,2-spirocyclohexachroman, 4-{N-[4-(2-nitrophenyl)-butyl]-3-aminomethyl}-4-hydroxy-2,2-spirocyclopentachroman, 4-{N-[4-(3-methoxy-4-hydroxy-5-nitrophenyl)-butyl]-aminomethyl}-4-hydroxy-2,2-spirocyclopentachroman, 4-{N-[4-(3-chloro-5-nitrophenyl)-butyl]-aminomethyl}-4-hydroxy-2,2-dimethylchroman, 4-{N-[4-(3-methyl-5-nitrophenyl)-butyl]-aminomethyl}-4-hydroxy-6,7-dimethyl-2,2-spirocyclopentachroman, 4-{N-[4-(4-methylsulphonylaminophenyl)-butyl]-aminomethyl}-4-hydroxy-6,7-dimethyl-2,2-spirocyclopentachroman, 4-{N-[4-(3-methoxy-5-methylsulphonylaminophenyl)-butyl]-aminomethyl}-4-hydroxy-2,2-spirocyclopentachroman, 4-{N-[4-(3-methyl-5-acetylaminophenyl)-butyl]-aminomethy}-4-hydroxy-2,2-spirocyclopentachroman, 4-{N-[1-(4-hydroxyphenyl)-2-methyl-isopropyl]-aminomethyl}-4-hydroxy-2,2-spirocyclopentachroman, 4-{N-[1-(3,5-dimethyl-4-methoxyphenyl)-2-methyl-isopropyl]-aminomethyl}-4-hydroxy-2,2-spirocyclopentachroman, 4-{N-[1-(3-nitro-4-methoxyphenyl)-2-methyl-isopropyl]-aminomethyl}-4-hydroxy-2,2-spirocyclopentachroman and 4-{N-[1-(3-methylsulphonylamino-4,5-dimethoxyphenyl))-2-methyl-isopropyl]-aminomethyl}-4-hydroxy-2,2-spirocyclopentachroman.

The invention furthermore relates to various processes for the preparation of the compounds of the formula (I). Either (A) amines of the formula (II)

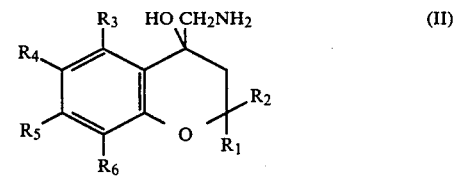

in which $R_1$, $R_2$, $R_3$, $R_4$, $R_5$ and $R_6$ have the meaning given above, are reacted with carbonyl compounds of the formula (III)

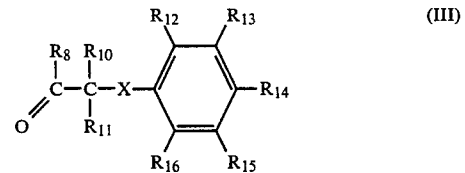

in which $R_8$ to $R_{16}$ have the meaning given above, with the proviso that X does not represent $NR_{17}$, in the presence of reducing agents, or (B) compounds of the formula (IV)

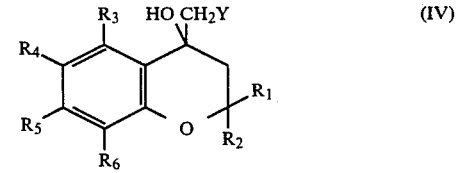

if necessary after isolation of the compounds which are formed by elimination of HY and are of the formula (Iva)

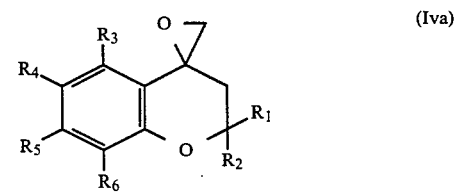

wherein, in the formulae (IV) and (Iva), $R_1$, $R_2$, $R_3$, $R_4$, $R_5$ and $R_6$ have the meaning given above and Y represents nucleophilically displaceable groups, such as alkyl-substituted or aryl-substituted sulphonyloxy groups, bromine or chlorine, are reacted with amines of the formula (V)

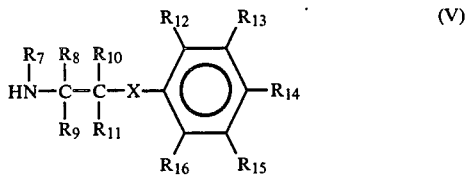

wherein $R_7$ to $R_{16}$ have the meaning given above, in the presence of an acid-binding agent.

Complex metal hydrides may be mentioned as examples of reducing agents which can be employed in process variant A. Alkali metal borohydrides, alkali metal cyanoborohydrides and/or alkali metal alanates, in particular sodium or lithium compounds, are preferred. Sodium borohydride, sodium cyanoborohydride and lithium alanate may be mentioned specifically. It is also possible to employ catalytically activated hydrogen at elevated pressures and temperatures.

The reducing agents can be employed in from equivalent amounts to an excess of 100%, preferably from equivalent amounts to an excess of 20%, relative to the carbonyl compound employed.

The acid-binding agents employed in preparation variant B are known bases. The following may be mentioned as examples: alkaline earth metal hydroxides or alkali metal hydroxides, such as sodium hydroxide and/or potassium hydroxide, alkaline earth metal carbonates or alkali metal carbonates, such as sodium bicarbonate or potassium carbonate, and organic nitrogen bases, such as triethylamine, tributylamine or benzyltrimethylammonium hydroxide.

These acid-binding agents can be used in from equivalent amounts to an excess of 100%, preferably in from equivalent amounts to an excess of 20%, relative to the halogen compound employed.

The reactions according to the invention are carried out in solvents. Suitable solvents are all solvents which are inert for the particular reaction, the following being preferably mentioned: alcohols, such as methanol, ethanol, isopropanol or tert.-butanol, ethers, such as diethyl ether, diisopropyl ether, tetrahydrofuran or dioxane, hydrocarbons, such as hexane, cyclohexane, benzene or toluene, chlorohydrocarbons, such as methylene chloride, chloroform, carbon tetrachloride or chlorobenzene, and furthermore acetonitrile, dimethylformamide, dimethyl sulphoxide or mixtures of these solvents.

The reaction temperatures can be varied within a relatively wide range. In general, the reaction is carried out at between $-50°$ and $150°$ C., preferably from $-10°$ to $120°$ C.

In carrying out the process according to the invention, 0.5 to 2 moles of the amine of the formula (V) or of the carbonyl compound of the formula (III) are preferably reacted per mol of the 4-hydroxychroman compounds of the formula (II) or of the formulae (IV) or (Iva).

The molar ratio of the reactants is particularly preferably 1:1. If an excess is used, it is preferable to employ an excess of the amine of the formula (V) or of the carbonyl compound of the formula (III).

The reaction products can be obtained by distillation, crystallization, evaporating down and recrystallizing, or chromatographic separation.

Some of the amines of the formula (V) which are employed in the preparation of the compounds according to the invention are known (see, for example, Arch. Pharm. 316, 193 (1983)), or can be obtained by analogous methods.

The following may be mentioned as examples of the amines of the formula (V): 1-(4-hydroxyphenyl)-2-methylisopropylamine, 1-(2-methoxy-4-hydroxyphenyl)-2-methylisopropylamine, 1-(2,6-dimethyl-4-hydroxyphenyl)-2-methylisopropylamine, 1-(2-chloro-4-hydroxyphenyl)-2-methylisopropylamine, 1-(3,5-dimethyl-4-methoxyphenyl)-2-methylisopropylamine, 1-(3,4,5-trimethoxyphenyl)-2-methyl-isopropylamine, 1-(2,6-dichloro-4-methoxyphenyl)-2-methylisopropylamine, 1-(3,5-dichloro-4-methoxy-phenyl)-2-methylisopropylamine, 2-amino-4-(3-nitrophenyl)-butane, 2-amino-4-(3-methylsulphonylaminophenyl)-butane, 2-amino-4-(4-methylsulphonylaminophenyl)-butane, 2-amino-4-(3-acetaminophenyl)-butane, 2-amino-4-(2-nitrophenyl)-butane, 2-amino-4-(3-N,N-dimethylaminosulphonylphenyl)-butane, 2-amino-4-(3-N-methylcarbamoylphenyl)-butane and 2-amino-4-(3,4-dimethoxy-5-methylsulphonylaminophenyl)-butane.

Some of the 4-hydroxy-chromanamines of the formula (II) which are employed in the preparation of the compounds according to the invention are known (J. med. Chem. 1982, 393), or can be prepared by analogous procedures.

The following process routes, starting from chroman-4-ones, may be represented by equations, by way of example:

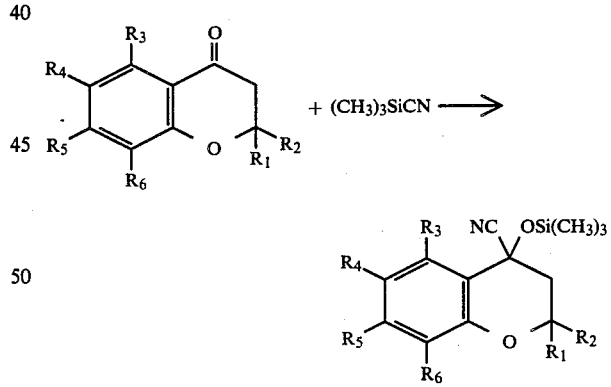

The 4-cyano-4-trimethylsilyloxychromans formed in this reaction can be hydrogenated with lithium aluminum hydride to give 4-aminomethyl-4-hydroxychromans, as shown in the following equation:

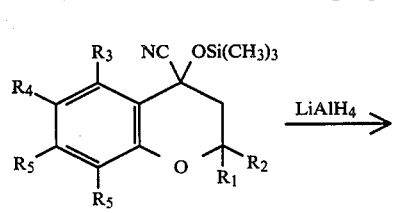

-continued

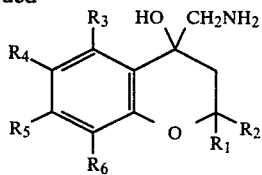

The following may be mentioned as examples of the 4-hydroxy-4-aminomethylchromans (II): 4-aminomethyl-4-hydroxy-chroman, 4-aminomethyl-4-hydroxy-2-methyl-chroman, 4-aminomethyl-4-hydroxy-2,2-dimethyl-chroman, 4-aminomethyl-4-hydroxy-2-propyl-chroman, 4-aminomethyl-4-hydroxy-2-isopropyl-chroman, 4-aminomethyl-4-hydroxy-2,2-diethyl-chroman, 4-aminomethyl-4-hydroxy-2-methyl-2-propyl-chroman, 4-aminomethyl-4-hydroxy-2-hexyl-chroman, 4-aminomethyl-4-hydroxy-2-cyclopentyl-chroman, 4-aminomethyl-4-hydroxy-2-cyclohexyl-chroman, 4-aminomethyl-4-hydroxy-2-spirocyclopentachroman, 4-aminomethyl-4-hydroxy-2-spirocyclohexachroman, 4-aminomethyl-4-hydroxy-6-methyl-2-spirocyclopentachroman, 4-aminomethyl-4-hydroxy-7-methyl-2-spirocyclopentachroman, 4-aminomethyl-4-hydroxy-6,8-dimethyl-2-spirocyclopentachroman, 4-aminomethyl-4-hydroxy-6-chloro-2-spirocyclopentachroman 4-aminomethyl-4-hydroxy-6-methoxy-2-spirocyclopentachroman, 4-aminomethyl-4-hydroxy-7-methoxy-2-spirocyclopentachroman, 4-aminomethyl-4-hydroxy-8-isopropoxy-2-spirocyclopentachroman, 4-aminomethyl-4-hydroxy-7-phenoxy-2-spirocyclopentachroman, 4-aminomethyl-4-hydroxy-7-benzyloxy-2-spirocyclopentachroman, 4-aminomethyl-4-hydroxy-7-phenyl-2-spirocyclopentachroman, 4-aminomethyl-4-hydroxy-6-methyl-2-spirocyclohexachroman, 4-aminomethyl-4-hydroxy-6-chloro-2-spirocyclohexachroman, 4-aminomethyl-4-hydroxy-7-methoxy-2-spirocyclohexachroman, 4-aminomethyl-4-hydroxy-6-methyl-2,2-dimethylchroman and 4-aminomethyl-4-hydroxy-7-methoxy-2,2-dimethylchroman.

The carbonyl compounds of the formula (III) which are used in the process according to the invention are known (see, for example, Beilsteins Handbuch der organischen Chemie (Beilstein's Handbook of Organic Chemistry) 6, 151, II 152; 7, 292, 303, 304, 314, I 154, 161, 162, 167, II 226, 233, 236, 243), or can be prepared by analogous methods.

The following may be mentioned as examples of the carbonyl compounds (III): phenylacetaldehyde, 3-chlorophenylacetaldehyde, 4-methylphenylacetaldehyde, 4-isopropylphenylacetaldehyde, 3-methoxyphenylacetaldehyde, 3,4-dimethoxyphenylacetaldehyde, 3,4-methylenedioxyphenylacetaldehyde, α-phenylpropionaldehyde, β-phenylpropionaldehyde, β-(4-chlorophenyl)-propionaldehyde, β-(4-trifluoromethylphenyl)-propionaldehyde, β-(3,4-dimethoxyphenyl)-propionaldehyde, β-(3,4-methylenedioxyphenyl)propionaldehyde, phenoxy-acetaldehyde, 4-chlorophenoxyacetaldehyde, 3,4-dimethylphenoxyacetaldehyde, 3,4-dimethoxyphenoxyacetaldehyde, phenylacetone, 3,4-dimethoxyphenylacetone, 3,4-methylenedioxyphenylacetone, benzylacetone, 4-(3-methylphenyl)-butan-2-one, 4-(4-methylphenyl)-butan-2-one, 4-(2-methylphenyl)butan-2-one, 4-(3-ethylphenyl)-butan-2-one, 4-(3-methyl-5-tert.-butylphenyl)-butan-2-one, 4-(3,5-di-tert.-butylphenyl)-butan-2-one, 4-(2,4-dimethylphenyl)-butan-2-one, 4-pentafluorophenylbutan-2-one, 4-(3-chloro-5-methylphenyl)-butan-2-one, 4-(2-chloro-3-methylphenyl)-butan-2-one, 4-(2,3,4-trimethoxyphenyl)-butan-2-one, 4-(3,4,5-trimethoxyphenyl)butan-2-one, 4-(3,5-di-isopropoxyphenyl)-butan-2-one, 4-(3-chloro-5-methoxyphenyl)-butan-2-one, 4-(3,4-methylene-dioxyphenyl)-butan-2-one, 4-(3,4-ethylenedioxyphenyl)-butan-2-one, 4-(2-naphthyl)-butan-2-one, 4-(3-methoxy-5-tert.-butylphenyl)-butan-2-one, 4-(3-trifluoromethylphenyl)-butan-2-one, 4-(3-benzyloxyphenyl)-butan-2-one, 4-(2-methyl-4-bromo-5-methoxyphenyl)-butan-2-one, 4-(3,5-dimethyl-4-methoxyphenyl)-butan-2-one, 4-(4-hydroxyphenyl)-butan-2-one, 4-(3-carbomethoxy-5-methoxyphenyl)-butan-2-one, 4-(3-carbamoylphenyl)-butan-2-one, 4-(4-carbamoylphenyl)-butan-2-one, 4-(4,5-dimethoxy-3-carbamoylphenyl)butan-2-one, 4-(3-methoxy-5-carbamoylphenyl)-butan-2-one, 4-(3-methyl-5-carbamoylphenyl)-butan-2-one, 4-(3-trifluoromethyl-5-carbamoylphenyl)-butan-2-one, 4-(2,4-dichloro-5-carbamoylphenyl)-butan-2-one, 4-(3,4-methylenedioxy-5-carbamoylphenyl)-butan-2-one, 4-(3-aminosulphonylphenyl)-butan-2-one, 4-(4-aminosulphonylphenyl)-butan-2-one, 4-(4,5-dimethoxy-3-aminosulphonylphenyl)-butan-2-one, 4-(3-4-(3-methoxy-5-aminosulphonylphenyl)-butan-2-one, 4-(3-methyl-5-aminosulphonylphenyl)-butan-2-one, 4-(3-trifluoromethyl-5-aminosulphonylphenyl)-butan-2-one, 4-(3-chloro-5-aminosulphonylphenyl)-butan-2-one, 4-(3,4-methylenedioxy-5-aminosulphonylphenyl)-butan-2-one, 4-(3-aminophenyl)-butan-2-one, 4-(3-N-methylaminophenyl)-butan-2-one, 4-(3-N,N-dimethylaminophenyl)-butan-2-one, 4-(3-N-succinimidophenyl)-butan-2-one, 4-(3-ethylsulphonylaminophenyl)-butan-2-one, 4-(3-n-butylsulphonylaminophenyl)-butan-2-one, 4-(3-N-methylmethylsulphonylaminophenyl)-butan-2-one, 4-(3-propionylaminophenyl)-butan-2-one, 4-(3-N-methylacetylaminophenyl)-butan-2-one, 4-(4-cyanophenyl)-butan-2-one, 4-(3-pyrrolidinophenyl)-butan-2-one, 1-(4-nitrophenoxy)-propan-2-one, 1-(3-nitrophenoxy)-propan-2-one, 1-(3-aminophenoxy)-propan-2-one, 1-(3-methylsulphonylaminophenoxy)-propan-2-one, 1-(4-N-methyl-methylsulphonylaminophenoxy)-propan-2-one, 1-(3-N-acetylaminophenoxy)-propan-2-one, 1-(3-N,N-dimethylaminosulphonylphenoxy)-propan-2-one, 1-(4-aminosulphonylphenoxy)-propan-2-one, 1-(4-carbamoyl-phenoxy)-propan-2-one, 4-(3-nitrophenyl)-butan-2-one, 4-(4-nitrophenyl)-butan-2-one, 4-(2-nitrophenyl)-butan-2-one, 4-(4,5-dimethoxy-3-nitrophenyl)butan-2-one, 4-(3-methoxy-5-nitrophenyl)-butan-2-one, 4-(3-methyl-5-nitrophenyl)-butan-2-one, 4-(3-trifluoromethyl-5-nitrophenyl)-butan-2-one, 4-(3-methoxy-4-hydroxy-5-nitrophenyl)-butan-2-one, 4-(3-chloro-5-nitrophenyl)-butan-2-one, 4-(3,4-methylenedioxy-5-nitrophenyl)-butan-2-one, 4-(3-methylsulphonylaminophenyl)-butan-2-one, 4-(4-methylsulphonylaminophenyl)-butan-2-one, 4-(4,5-dimethoxy-3-methylsulphonylaminophenyl)-butan-2-one, 4-(3-methoxy-5-methylsulphonylaminophenyl)-butan-2-one, 4-(3-methyl-5-methylsulphonylaminophenyl)-butan-2-one, 4-(3-trifluoromethyl-5-methylsulphonylaminophenyl)-butan-2-one, 4-(3,5-bis-methylsulphonylaminophenyl)-butan-2-one, 4-(3-methoxy-4-hydroxy-5-methylsulphonylaminophenyl)-butan-2-one, 4-(3,4-methylenedioxy-5-methylsulphonylaminophenyl)-butan-2-one, 4-(3-acetylaminophenyl-butan-2-one, 4-(4-acetylaminophenyl)-butan-2-one, 4-(4,5-dimethoxy-3-acetylaminophenyl)-butan-2-one, 4-(3-methoxy-5-acetylaminophenyl)-butan-2-one, 4-(3-methyl-5-acetylaminophenyl)-butan-2-one, 4-(3-trifluoromethyl-5-acetylaminophenyl)-butan-2-one and 4-(3,4-methylenedioxy-5-acetylaminophenyl)-butan-2-one.

The compounds of the formulae (IV) and (Iva) which are employed in the preparation of the compounds according to the invention according to variant B were hitherto unknown. They can be prepared by known methods, for example by hydrolysis of the known 4-cyano-4-trimethylsilyloxy-chromans (see J. med. Chem. 1982, 393) to give the α-hydroxycarboxylic acid or ester, followed by reduction to the diol and conversion to compounds of the formula (IV) or (Iva).

The 4-hydroxy-chroman derivatives according to the invention surprisingly have an antihypertensive action and can therefore be employed, in the free form or in the form of their pharmaceutically acceptable acid addition salts, as medicaments.

The new compounds have a broad and varied pharmacological action spectrum and a surprisingly long duration of action.

Specifically, it has been possible to demonstrate the following principal actions in animal experiments:

1. The tone of the smooth muscle of the vessels is greatly reduced under the action of the compounds. This vascular-spasmolytic action can take place in the entire vascular system or can manifest itself more or less isolated in circumscribed vascular regions. The compounds are therefore particularly suitable as cerebral therapeutic agents.

2. The compounds lower the blood pressure of normotonic and hypertonic animals and can thus be used as antihypertensive agents.

The compounds according to the invention are particularly suitable for the therapy of hypertension and for the treatment of cerebral and peripheral disfunctions and cerebral and peripheral disturbances of blood flow.

The new active compounds can be converted in a known manner into the customary formulations, such as tablets, capsules, dragees, pills, granules, aerosols, syrups, emulsions, suspensions and solutions, using inert, non-toxic, pharmaceutically suitable excipients or solvents. The therapeutically active compounds should in each case be present in a concentration of about 0.5 to 90% by weight of the total mixture, that is to say in amounts which suffice to achieve the indicated dosage range.

The formulations are prepared, for example, by extending the active compounds with solvents and/or excipients, using emulsifiers and/or dispersing agents if appropriate, and, for example in the case of water being employed as the diluent, organic solvents can be used as auxiliary solvents if appropriate.

As examples of auxiliary substances there may be mentioned: water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid excipients such as, for example, natural rock powders (for example kaolins, aluminas, talc and chalk), synthetic rock powders (for example highly disperse silica and silicates), and sugars (for example raw sugar, lactose and glucose), emulsifiers (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium lauryl-sulphate).

Administration is effected in the customary manner, preferably orally or parenterally, especially perlingually or intravenously. In the case of oral use, tablets can of course also contain, in addition to the excipients mentioned, additives such as sodium citrate, calcium carbonate and dicalcium phosphate, together with various further substances such as starch, preferably potato starch, gelatine and the like. Furthermore, lubricants such as magnesium stearate, sodium lauryl-sulphate and talc can be used conjointly for tablet-making. In the case of aqueous suspensions and/or elixirs which are intended for oral use the active compounds can be mixed with various flavor-improving agents or dyestuffs in addition to the abovementioned auxiliaries.

In the case of parenteral application, solutions of the active compounds can be employed, using suitable liquid excipients.

In general it has proved advantageous, in the case of intravenous administration, to administer amounts of about 0.001 to 1 mg/kg, preferably about 0.01 to 0.5 mg/kg of body weight daily to achieve effective results, whilst in the case of oral administration the dosage is about 0.05 to 20 mg/kg, preferably 0.1 to 10 mg/kg of body weight daily.

Nevertheless it can at times be necessary to deviate from the amounts mentioned and in particular to do so as a function of the body weight of the test animal or of the nature of the administration route, but also because of the type of animal and its individual behaviour towards the medicine or the nature of its formulation and the time or interval at which it is administered. Thus it may suffice, in some cases, to manage with less than the abovementioned minimum amount while in other cases the upper limit mentioned must be exceeded. Where major amounts are administered it can be advisable to divide these into several administrations over the course of the day. The same dosage range is envisaged for administration in human medicine. Here, again, the general sense of the above comments applies.

EXAMPLES ACCORDING TO THE INVENTION

Preparation according to variant A

EXAMPLE 1

A mixture of 7 g of 2,2-spirocyclopenta-4-hydroxy-4-aminomethylchroman, 6.5 g of 4-(m-trifluoromethylphenyl)-butan-2-one and 70 ml of toluene is heated to 115° C. for 1 hour in a water separator. Thereafter, the solution is evaporated down, the residue is diluted with 150 ml of absolute tetrahydrofuran, and 5 g of lithium aluminum hydride are added in portions at 20° C. The mixture is stirred for 4 hours at the reflux temperature, after which it is cooled, and carefully stirred with 5 ml of water and 15 ml of 15 per cent strength potassium hydroxide solution at about 0° C. The mixture is then filtered under suction, the filtrate is evaporated down and the residue is distilled at 250° C./0.03 mm Hg. The nuclear resonance spectrum is in agreement with the structure of 4-{N-[4-(3-trifluoromethylphenyl)-2-butyl]-aminomethyl}-4-hydroxy-2,2-spirocyclopentachroman. Yield: 68% of theory.

EXAMPLE 2

The procedure described in Example 1 is followed, except that 7.5 g of 4-(m-trifluoromethyl-p-chlorophenyl)-butan-2-one are used as the ketone. After the elimination of water, the toluene solution of the imine formed as an intermediate is evaporated down, the residue is dissolved in 150 ml of methanol, and 5 g of sodium borohydride are added to this solution in the course of 2 hours. After 2 days, the solution is evaporated down, and water and toluene (150 ml of each) are added. The organic phase is evaporated down, and the residue is distilled in a bulb tube. 9.5 g of 4-{N-[4-(3-trifluoromethyl-4-chlorophenyl)-2-butyl]-aminomethyl}-4-hydroxy-2,2-spirocyclopentachroman are obtained. Boiling point 250°/0.04 mm Hg. Yield: 62% of theory.

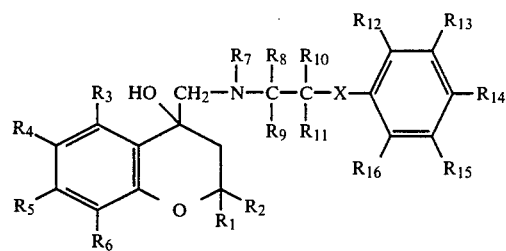

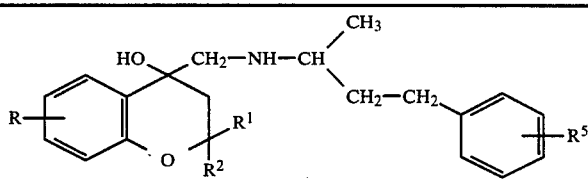

| Example No. | R | $R^1/R^2$ | $R^5$ | Boiling Point |
|---|---|---|---|---|
| 3 | H | —(CH$_2$)$_4$— | 3,5-(CF$_3$)$_2$ | 230–250° C./0.05 mm Hg |
| 4 | H | —(CH$_2$)$_4$— | 3,5-(CH$_3$O)$_2$ | 250–260° C./0.05 mm Hg |
| 5 | H | —(CH$_2$)$_4$— | 3,5-(CH$_3$)$_2$ | 240–250° C./0.02 mm Hg |
| 6 | H | —(CH$_2$)$_4$— | 3-CH$_3$/5-t-C$_4$H$_9$ | 250° C./0.03 mm Hg |
| 7 | H | —(CH$_2$)$_5$— | 3-CH$_3$/5-t-C$_4$H$_9$ | 240° C./0.02 mm Hg |
| 8 | H | —(CH$_2$)$_5$— | 3,4-O—CH$_2$—O | 250° C./0.02 mm Hg |
| 9 | 6,7-(CH$_3$)$_2$ | —(CH$_2$)$_4$— | 3,5-(CH$_3$O)$_2$ | 260–70° C./0.02 mm Hg |
| 10 | 6,7-(CH$_3$)$_2$ | —(CH$_2$)$_4$— | 3,4-O—CH$_2$—O | 250–60° C./0.02 mm Hg |
| 11 | 6,7-(CH$_3$)$_2$ | —(CH$_2$)$_4$— | 3-CH$_3$/5-t-C$_4$H$_9$ | 260° C./0.02 mm Hg |
| 12 | 6,7-(CH$_3$)$_2$ | —(CH$_2$)$_4$— | 3-CF$_3$ | 250° C./0.04 mm Hg |
| 13 | H | —(CH$_2$)$_4$— | 3,4-O—CH$_2$—O | 240–50° C./0.04 mm Hg |
| 14 | H | —(CH$_2$)$_5$— | 3,4,5-(CH$_3$O)$_3$ | 270° C./0.02 mm Hg |
| 15 | 6,7-(CH$_3$)$_2$ | —(CH$_2$)$_4$— | 3,4,5-(CH$_3$O)$_3$ | 275° C./0.02 mm Hg |
| 16 | H | —(CH$_2$)$_4$— | 3,4,5-(CH$_3$O)$_3$ | 260–70° C./0.03 mm Hg |
| 17 | 6-CH$_3$O | —(CH$_2$)$_4$— | 3-CF$_3$ | 250° C./0.05 mm Hg |
| 18 | 7-Cl | (CH$_3$)$_2$ | 3-CH$_3$/5-t-C$_4$H$_9$ | 240° C./0.03 mm Hg |
| 19 | 6,8-(CH$_3$)$_2$ | (CH$_3$)$_2$ | 3-CF$_3$ | 230° C./0.02 mm Hg |
| 20 | H | —(CH$_2$)$_4$— | 3-SO$_2$(CH$_3$)$_2$ | oil[1] |
| 21 | H | —(CH$_2$)$_4$— | 3-CONHCH$_3$ | oil[1] |
| 22 | 6,7-(CH$_3$)$_2$ | —(CH$_2$)$_5$— | 3-CONH$_2$ | oil[1] |
| 23 | H | (CH$_3$)$_2$ | 3-SO$_2$NH$_2$ | oil[1] |
| 24 | H | —(CH$_2$)$_4$— | 3-SO$_2$NH$_2$/4-CH$_3$O | oil[1] |
| 25 | H | —(CH$_2$)$_4$— | 3-NO$_2$ | 225–235° C./0.04 mm Hg |
| 26 | H | —(CH$_2$)$_4$— | 3-NO$_2$/5-OCH$_3$ | oil[1] |
| 27 | H | —(CH$_2$)$_4$— | 4-NO$_2$ | 250° C./0.03 mm Hg |
| 28 | H | —(CH$_2$)$_4$— | 2-NO$_2$/3,4-O—CH$_2$—O— | (172–175° C. (Fumarat)) |
| 29 | H | —(CH$_2$)$_4$— | 3-NH$_2$ | (119–123° C. (Maleinat)) |
| 30 | H | —(CH$_2$)$_4$— | 3-NH—COCH$_3$ | oil[1] |
| 31 | H | —(CH$_2$)$_4$— | 3-N(CH$_3$)COCH$_3$ | oil[1] |
| 32 | H | —(CH$_2$)$_4$— | 3-NHSO$_2$CH$_3$ | (218–221° C. (Hydrochlorid)) |
| 33 | H | —(CH$_2$)$_4$— | 3-NHSO$_2$n-C$_4$H$_9$ | (119–126° C. (Fumarat)) |
| 34 | H | —(CH$_2$)$_4$— | 3-NHSO$_2$CH$_3$/5-OCH$_3$ | oil[1] |
| 35 | H | —(CH$_2$)$_4$— | 2-NHSO$_2$CH$_3$/4,5-O—CH$_2$—O— | (149–151° C. (Maleinat)) |
| 36 | H | —(CH$_2$)$_4$— | 3-N(CH$_3$)SO$_2$CH$_3$ | (169–171° C. (Fumarat)) |
| 37 | H | —(CH$_2$)$_4$— | 3-CH$_3$/5-NHSO$_2$CH$_3$ | oil[1] |
| 38 | H | —(CH$_2$)$_4$— | 3-NH—COC$_2$H$_5$ | oil[1] |
| 39 | H | —(CH$_2$)$_4$— | 3-NH—CONHCH$_3$ | oil[1] |
| 40 | H | —(CH$_2$)$_4$— | 3-NH—CO$_2$CH$_3$ | oil[1] |

[1]Chromatographed over silica gel using CH$_2$Cl$_2$/acetone mixtures.

It is understood that the specification and examples are illustrative but not limitative of the present invention and that other embodiments within the spirit and scope of the invention will suggest themselves to those skilled in the art.

We claim:
1. A substituted 4-hydroxybenzopyran of the formula in which
$R_1$ and $R_2$ are identical or different and represent hydrogen, alkyl or cycloalkyl,
or in which
$R_1$ and $R_2$, together with the carbon atom between them, form a carbocyclic ring selected from the group consisting of cyclopropane, cyclobutane, cyclopentane, cyclohexane, cycloheptane, cyclononane, cyclodecane and cyclododecane,
$R_3$, $R_4$, $R_5$ and $R_6$ are identical or different and represent hydrogen, hydroxyl, halogen, alkyl cycloalkyl, phenyl, phenyl mono- or di-substituted by $C_1$–$C_4$-alkyl, halogen and/or $C_1$–$C_4$-alkoxy, phenyl-$C_1$–$C_8$-alkyl, phenyl-$C_1$–$C_8$-alkyl mono- or di-substituted on the phenyl radical by $C_1$–$C_4$-alkyl, halogen and/or $C_1$–$C_4$-alkoxy, alkoxy, and phenylalkoxy selected from the group consisting of benzyloxy, phenylethoxy, phenylpropoxy, phenylisopropoxy, phenylbutoxy and phenyisobutoxy, $R_7$, $R_8$, $R_9$, $R_{10}$ and $R_{11}$ are identical or different and represent hydrogen or alkyl, X represents a single bond, or methylene which is unsubstituted or substituted by one or two alkyl groups, or represents oxygen or $NR_{17}$, wherein $R_{17}$ represents hydrogen and alkyl having up to 6 carbon atoms, $R_{12}$, $R_{13}$, $R_{14}$, $R_{15}$, and $R_{16}$ are identical or different and each represent hydrogen, hydroxyl, halogen, alkyl, cycloalkyl, alkoxy, aralkoxy selected from the group consisting of benzyloxy, phenylethoxy, phenylpropoxy, phenylisopropoxy, phenylbutoxy and phenyisobutoxy, trifluoromethyl, nitro, cyano or the

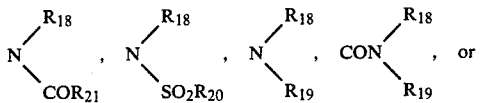

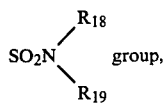

wherein $R_{18}$ and $R_{19}$ are identical or different and each represent hydrogen or unsubstituted or halogen-substituted alkyl, and wherein $R_{20}$ represents unsubstituted or halogen-substituted alkyl, and wherein $R_{21}$ represents hydrogen, unsubstituted or halogen-substituted alkyl, unsubstituted or halogen-substituted alkoxy or unsubstituted or halogen-substituted alkylamino, and $R_{12}$ and $R_{13}$ or $R_{13}$ and $R_{14}$ together optionally each represent an alkylenedioxy group or the group —CH=CH—CH=CH—, or a pharmaceutically acceptable addition salt thereof.

2. A compound or salt according to claim 1, in which $R_1$ and $R_2$ are identical or different and represent hydrogen, $C_1$–$C_6$-alkyl or $C_5$–$C_7$-cycloalkyl, or $R_1$ and $R_2$, together with the included C atom of the chroman ring, form a 4- to 7-membered saturated carbocyclic ring;

$R_3$ to $R_6$ are identical or different and represent hydrogen, hydroxyl, halogen, $C_1$–$C_6$-alkyl, $C_5$–$C_7$-cycloalkyl, phenyl unsubstituted or monosubstituted or disubstituted by $C_1$–$C_4$-alkyl, halogen and/or $C_1$–$C_4$-alkoxy, or $C_7$–$C_9$-phenylalkyl, the phenyl radical of which is unsubstituted or monsubstituted or disubstituted by $C_1$–$C_4$-alkyl, halogen and/or $C_1$–$C_4$-alkoxy;

$R_7$, $R_8$, $R_9$, $R_{10}$ and $R_{11}$ are identical or different and represent hydrogen or $C_1$–$C_6$-alkyl, X represents a single bond, or methylene which is unsubstituted or monosubstituted or disubstituted by $C_1$–$C_4$-alkyl, or represents oxgyen or —$NR_{17}$, wherein $R_{17}$ represents hydrogen or $C_1$–$C_4$-alkyl, $R_{12}$, $R_{13}$, $R_{14}$, $R_{15}$ and $R_{16}$ are identical or different and each represent hydrogen, hydroxyl, chlorine, fluorine, alkyl having 1–4 C atoms, alkoxy having 1 to 3 C atoms, phenylalkoxy having up to 8 C atoms, trifluoromethyl, nitro, cyano or the

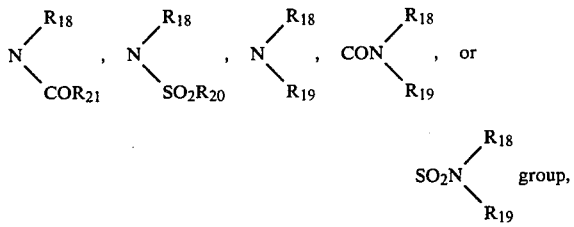

wherein $R_{18}$ and $R_{19}$ are identical or different and each represent hydrogen or alkyl having 1–4 C atoms which is unsubstituted or monosubstituted to trisubstituted by halogen, $R_{20}$ represents alkyl having 1–6 C atoms which is unsubstituted or monsubstituted to trisubstituted by halogen, and $R_{21}$ represents hydrogen, alkyl, alkoxy or alkylamino, each having 1–4 C atoms per alkyl and alkoxy group, the alkyl radical being unsubstituted or monosubstituted to trisubstituted by halogen, and $R_{12}$ and $R_{13}$ or $R_{13}$ and $R_{14}$ together optionally represent an alkylenedioxy group having 1 or 2 C atoms or the group —CH=CH—CH=CH—.

3. A compound or salt according to claim 1, in which $R_1$ and $R_2$ are identical or different and represent hydrogen, $C_1$–$C_4$-alkyl, or, together with the carbon atom between them, form a saturated carbocyclic $C_5$ or $C_6$ ring, $R_3$ to $R_6$ are identical or different and denote hydrogen, hydroxyl, $C_1$–$C_4$-alkyl, $C_1$–$C_4$-alkoxy or chlorine, $R_7$ to $R_{11}$ are identical or different and represent hydrogen or $C_1$–$C_4$-alkyl, X represents a single bond, oxygen, methylene or —$NR_{17}$, $R_{17}$ denotes hydrogen or $C_1$–$C_3$-alkyl, and $R_{12}$ to $R_{16}$ are identical or different and denote hydrogen, chlorine, cyclohexyl, $C_1$–$C_4$-alkyl, $C_1$–$C_3$-alkoxy, aralkoxy phenylalkoxy having up to 8 C atoms, trifluoromethyl, nitro, cyano or the

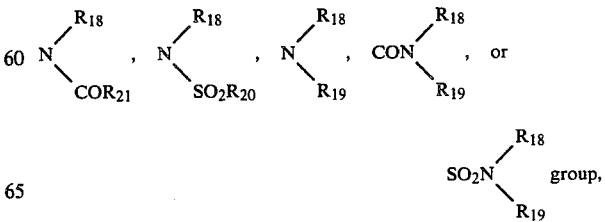

wherein $R_{12}$ and $R_{13}$ or $R_{13}$ and $R_{14}$ together each optionally form a methylenedioxy group or a —CH=CH—CH=CH— group, and wherein $R_{18}$ and $R_{19}$ are identical or different and each represent hydrogen or alkyl having 1-4 C atoms which is unsubstituted or substituted by fluorine or chlorine, and wherein $R_{20}$ represents alkyl having 1-4 C atoms which is unsubstituted or substituted by fluorine or chlorine, and wherein $R_{21}$ represents hydrogen, unsubstituted or fluorine-substituted or chlorine-substituted alkyl having 1-4 C atoms, alkoxy or alkylamino, each having 1-2 C atoms.

4. A compound according to claim 1, wherein such compound is 4-{N-[4-(3,5-di-methoxyphenyl)-2-butyl]-aminomethyl}-4-hydroxy-2,2-spirocyclopentachroman of the formula

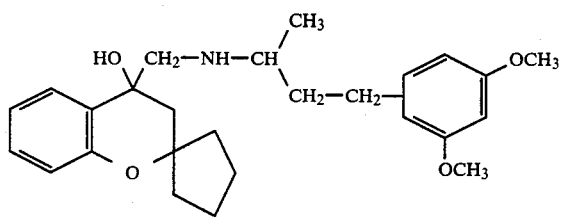

or a pharmaceutically acceptable addition salt thereof.

5. A compound according to claim 1, wherein such compound is 4-{N-[4-(3,4-methylenedioxyphenyl)-2-butyl]-aminomethyl}-4-hydroxy-2,2-spirocyclopentachroman of the formula

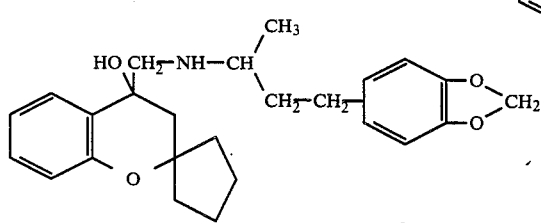

or a pharmaceutically acceptable addition salt thereof.

6. A compound according to claim 1, wherein such compound is 4-{N-[4-(3,4,5-trimethoxyphenyl)-2-butyl]-aminomethyl}-4-hydroxy-2,2-spirocyclohexachroman of the formula

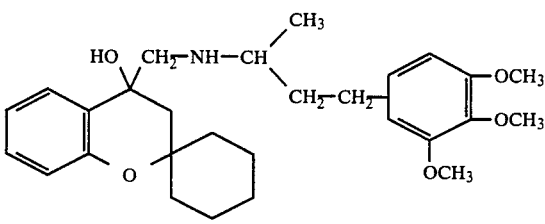

or a pharmaceutically acceptable addition salt thereof.

7. A compound according to claim 1, wherein such compound is 4-{N-[4-(3,4,5-1 -trimethoxyphenyl)-2-butyl]-aminomethyl}-4-hydroxy-2,2-spirocyclopentachroman of the formula

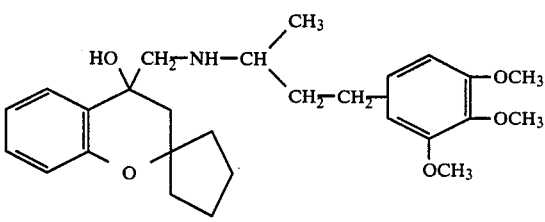

or a pharmaceutically acceptable addition salt thereof.

8. A compound according to claim 1, wherein such compound is 4-{N-[4-(3-methoxy-5-methylsulphonamido-phenyl)-2-butyl]-aminomethyl}-4-hydroxy-2,2-spirocyclopentachroman of the formula

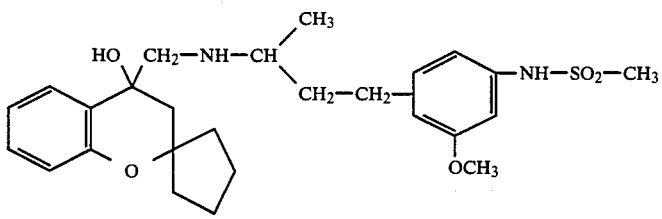

or a pharmaceutically acceptable addition salt thereof.

9. A compound according to claim 1, wherein such compound is 4-{N-[4-(3-N-methyl-methylsulphonamidophenyl)-2-butyl]-aminomethyl}-4-hydroxy-2,2-spirocyclopentachroman of the formula

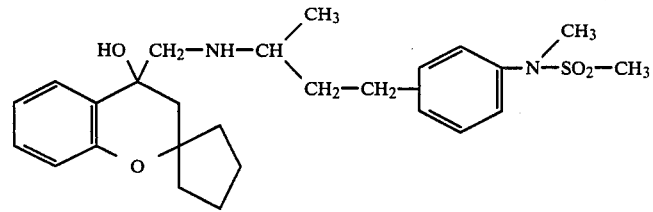

or a pharmaceutically acceptable addition salt thereof.

10. A blood circulation active composition comprising a blood circulation active-effective amount of a compound or salt according to claim 1 in admixture with a diluent.

11. A unit dose of a composition according to claim 10 in the form of a tablet, capsule or ampule.

12. A method of modifying the blood circulation of a patient in need thereof which comprises administering to such patient a blood circulation active-effective amount of a compound or salt according to claim 1.

13. The method according to claim 12, wherein such compound is

4-{N-[4-(3,5-di-methoxyphenyl)-2-butyl]-aminomethyl}-4-hydroxy-2,2-spirocyclopentachroman, 4-{N-[4-(3,4-methylenedioxyphenyl)-2-butyl]-aminomethyl}-4-hydroxy-2,2-spirocyclopentachroman, 4-{N[4-(3,4,5-trimethoxyphenyl)-2-butyl]-aminomethyl}-4-hydroxy-2,2-spirocyclohexachroman, 4-{N-[4-(3,4,5-trimethoxyphenyl)-2-butyl]-aminomethyl}-4-hydroxy-2,2-spirocyclopentachroman, 4-{N-[4-(3-methoxy-5-methylsulphonamido-phenyl)-2-butyl]-aminomethyl}-4-hydroxy-2,2-spirocyclopentachroman or 4-{N-[4-(3-N-methyl-methylsulphonamidophenyl)-2-butyl]-aminomethyl}-4-hydroxy-2,2-spirocyclopentachroman, or a pharmaceutically acceptable addition salt thereof.

* * * * *